United States Patent [19]
Fujise et al.

[11] B 3,989,756
[45] Nov. 2, 1976

[54] PROCESS FOR THE PRODUCTION OF HALOGENATED AROMATIC PRIMARY AMINES

[75] Inventors: Masatomo Fujise, Wako; Yasuo Nakano, Tokyo; Koji Isobe, Yono, all of Japan

[73] Assignee: Nippon Kayaku Kabushiki Kaisha, Tokyo, Japan

[22] Filed: Sept. 6, 1974

[21] Appl. No.: 503,742

[44] Published under the second Trial Voluntary Protest Program on February 17, 1976 as document No. B 503,742.

[30] Foreign Application Priority Data
Sept. 6, 1973 Japan.............................. 48-100541

[52] U.S. Cl................................ 260/580; 260/689
[51] Int. Cl.²........................................ C07C 85/11
[58] Field of Search................. 252/477 Q; 260/689, 260/690, 580, 551 C

[56] References Cited
UNITED STATES PATENTS 2,214,067  9/1940  Petersen................... 260/551 C UX
3,145,231  8/1964  Kosak............................ 260/690 X

FOREIGN PATENTS OR APPLICATIONS 708,699    5/1954  United Kingdom.............. 260/570.5
1,191,610  5/1970  United Kingdom................ 260/580

*Primary Examiner*—Allen B. Curtis
*Attorney, Agent, or Firm*—Russell & Nields

[57] ABSTRACT

Process for producing halogenated aromatic primary amines that may contain substituents such as methyl, ethyl, methoxy, and so on, by catalytic hydrogenation of halogenated aromatic nitro compounds in the presence both of a Raney nickel catalyst and of a dehalogenation inhibitor selected from the group consisting of dicyandiamide, cyanamide and calcium cyanamide, in an inert solvent at a temperature in the range from 40° to 150° C under an elevated hydrogen pressure, whereby any dehalogenated aromatic primary amine impurity in the halogenated aromatic primary amine product is held to an acceptable minimum so that the halogenated aromatic amines may be produced in a high state of purity.

8 Claims, No Drawings

PROCESS FOR THE PRODUCTION OF HALOGENATED AROMATIC PRIMARY AMINES

BACKGROUND OF THE INVENTION

1. Field of the Invention

This invention relates to the production of halogenated aromatic primary amines from the corresponding halogenated aromatic nitro compounds, the term "halogen" being used throughout this specification and claims to mean chlorine or bromine, so that the terms "halogenated" and "dehalogenation" mean "chlorinated or brominated" and "dechlorination or debromination" respectively.

2. Background of the Invention Prior Art

In the prior art process of producing halogenated aromatic primary amines, the corresponding halogenated nitro compounds are hydrogenated in the presence of Raney nickel catalyst. However, the desired hydrogenation reaction is accompanied by undesired dehalogenation, so that dehalogenated aromatic primary amines are formed as undesired by-products.

Therefore, one inevitable disadvantage of this dehalogenation had been that the yield and purity of the product is deteriorated. Indeed, the undesired by-products are made up primarily of dehalogenated aromatic primary amines. Fractional distillation is needed to eliminate them from halogenated aromatic primary amine, especially when the impurity content should be restricted.

Moreover, during the dehalogenation reaction hydrochloric acid is produced and the reaction mixture is thus made acidic, so that the surface of the Raney nickel catalyst is dissolved and the activity of the catalyst is extensively damaged, spoiling its usefulness.

Although many processes have been investigated to solve these problems, prior to our invention no practical solution was discovered. A platinum or palladium catalyst supported on carbon is mentioned in some patents. But such metals are very expensive.

A process for preparing halogenated aromatic amines by hydrogenation of the corresponding nitro-compounds using Raney Nickel catalyst in the presence of alkylamines, alkanolamines, basic heterocyclic compounds involving nitrogen atoms and alicyclic amines is described in Japanese provisional publication No. 49728/1973. However, the effectiveness of this previously described process is small as compared with our invention.

A process for preparing halogenated aromatic amines by hydrogenating the corresponding nitro compounds over a Raney nickel catalyst containing a thiocyanate is described in British Patent No. 1,191,610. But in this process, it takes a long time to hydrogenate the nitro compounds and activity of the catalyst is badly impaired by hydrogenation.

In Japanese patent provisional publication No. 49728/73 and U.S. Pat. No. 3,067,253, relatively low reaction temperatures, for example 22 ~ 40°C or 55 ~ 60°C, were employed to prevent dehalogenation. Some organic (Japanese patent provisional publication No. 49728/1973) and inorganic (U.S. Pat. No. 3,067,253) basic compounds mentioned in these patents were effective to some extent for hydrogenation at a lower temperature, but they are not useful at higher temperatures which are advantageous for industrial production. For example, in the hydrogenation of 2.5-dichloroaniline in the presence of Raney nickel and monoethanolamine, 3 percent of aniline and 2 percent of m- and 0-chloroaniline were detected by gas chromatography.

DETAILED DESCRIPTION OF THE INVENTION

After much experimental research in our laboratory, a new advantageous process has been discovered as follows. In this invention, hydrogenation of halogenated aromatic nitro compounds using Raney nickel catalyst is carried out very smoothly by using a dehalogenation inhibitor.

Many kinds of halogenated aromatic nitro compounds are reduced to corresponding halogenated aromatic primary amines in nearly theoretical yield.

Specific examples of the halogenated aromatic primary amines are as follows.

bromoanilines for example o-, m- and p- bromoaniline
chloroanilines for example o-, m- and p- chloroaniline
dichloroanilines for example 2,3-, 3,4- and 2,5- dichloroaniline
trichloroanilines for example 2,3,4, or 2,4,5- trichloroaniline
dichlorodiaminobenzenes for example 3,4-dichloro-1, 6-diaminobenzene, 2,5-dichloro1-, 4-diaminobenzene
chlorotoluidines for example 4 or 6-chloro-1-methyl-2-aminobenzene, 2 or 6-chloro-1-methyl-4-aminobenzene
chloroethylanilines for example 4 or 6-chloro-1-ethyl-2-aminobenzene, 2 or 3-chloro-1-ethyl-4-aminobenzene,
chloromethoxy anilines for example 4 or 6-chloro-1-methoxy-2-aminobenzene, 2 or 3-chloro-1-methoxy-4-aminobenzene
diaminochlorobenzene for example 2,4-diamino-1-chlorobenzene
chloroaminophenol for example 4- or 5- chloro-2-aminophenol They are produced from corresponding halogenated aromatic nitro compounds such as o-, m- and p- chloronitrobenzene, o-, m-, and p- bromonitrobenzene, 2,3-, 3,4- and 2,5 dichloronitrobenzene, 2,3,4 or 2,4,5- trichloro nitrobenzene, 3,4-dichloro-6-nitroaniline, 2,5-dichloro-4-nitroaniline,
4 or 6-chloro-1-methyl-2-nitrobenzene,
2 or 6-chloro-1-methyl-4-nitrobenzene,
4 or 6-chloro-1-ethyl-2-nitrobenzene,
2 or 6-chloro-1-ethyl-4-nitrobenzene,
4 or 6-chloro-1-methoxy-2-nitrobenzene,
2 or 6-chloro-1-methoxy-4-nitrobenzene,
2,4-dinitro-1-chlorobenzene,
4- or 5- chloro-2-nitrophenol, The dehalogenation inhibitor of the invention is selected from the group consisting of dicyanidiamide, cyanamide and calcium cyanamide. Its superior dehalogenation inhibiting effect on the catalytic hydrogenation has not been expected by any past knowledge at all including prior art disclosures using dehalogenation inhibitors.

Whenever the dehalogenation inhibitors of the invention (i.e. decyandiamide, cyanamide and calcium cyanamide, especially dicyandiamide) are used the hydrogenation proceeds with desirable reaction velocity. By this invention, a reasonable reaction velocity for technical hydrogenation is available and hardly any dehalogenated aromatic primary amine is found in the product. More concretely, in many instances of hydrogenation of halogenated aromatic nitro compounds in accordance with the invention, dehalogenation is less than 0.1 percent. The activity of the catalyst is not practically impaired by such hydrogenation. Therefore, the consumption of the catalyst in such hydrogenation is very small. Moreover, Raney nickel catalyst is inexpensive. These facts make it advantageous to apply the present invention to industrial production.

By this new process, practically pure halogenated aromatic primary amine is produced from corresponding nitro compounds.

The hydrogenation temperature may vary from 40 to 150°C but a better temperature range for operation is 50° ~ 130°C.

In our invention any dehalogenated by-product can be reduced to less than 0.1 percent of the reaction product even at relatively high reaction temperatures such as from 100° to 130°C, and under optimum conditions the dehalogenated by-product is less than 0.02 percent. The hydrogenation is carried out by known techniques in the presence of an inert solvent, continuously or in batches, at an elevated hydrogen pressure, preferably 1 to 100 kg/cm$^2$ (absolute).

In this invention, the yield of a halogenated aromatic primary amine is almost theoretical. When the dehalogenation inhibitor of this invention is used, the hydrogenation velocity is almost the same as in the case of hydrogenation of an aromatic nitro compound which is not substituted with a halogen atom.

The activity of the catalyst is scarcely impaired by repeated hydrogenation. The catalyst can be used repeatedly for successive hydrogenations. The catalyst consumption is practically the same as in the case of hydrogenation of an unsubstituted aromatic nitro compound. It is recommended that an inert solvent be used for the hydrogenation in this invention. For example, methanol is a suitable solvent. Ethanol, isopropanol, dioxane and tetrahydrofuran can also be used. A lower aliphatic alcohol-water mixture can also be used. In some cases of hydrogenation, water may be used as a solvent. The inert solvent is usually used in the range from 0.3 to 10 times the weight of the halogenated aromatic nitro compound.

Raney nickel catalyst is very suitable for technical hydrogenation of halogenated aromatic nitro compounds and is available in the commercial market. The Raney nickel is used preferably in a concentration from 0.5 to 20 percent by weight of the halogenated nitro compounds.

Dicyandiamide and calcium cyanamide have been made industrially and can be purchased. Cyanamide is an unstable compound and is converted into dicyandiamide by heating in a weak alkaline solution. Dicyandiamide, cyanamide or calcium cyanamide can be dissolved or suspended in an inert solvent. Dicyandiamide, orcyanamide is used preferably in the range from 0.03 to 30 percent, more preferably from 0.1 to 10 percent by weight of the halogenated aromatic nitro compound, and calcium cyanamide is used preferaby in the range from 0.1 to 30 percent, more preferably from 0.3 to 10 percent.

Satisfactory results are obtained by the following general hydrogenation procedure.

Alkali-treated Raney nickel water paste, inert solvent (for example methanol) and dehalogenation inhibitor (for example dicyandiamide) are introduced into an autoclave. Then a halogenated aromatic nitro compound is added. The autoclave is closed and the air therein is replaced with nitrogen and then with hydrogen. The hydrogen pressure is elevated. The mixture is stirred and heated to the reaction temperature and hydrogenated. The reaction temperature is maintained constant by cooling the reacting mixture and hydrogen is continuously fed to maintain the pressure constant.

In industrial production, good results are obtained by the following procedure.

Raney nickel water paste, methanol and dicyandiamide are introduced in an autoclave.

After nitrogen displacement nitrogen is displaced with hydrogen. The hydrogen pressure is elevated to 1 ~ 100 kg/cm$^2$. The agitator in the autoclave is started. Temperature is set to 50 ~ 130°C. A molten halogenated aromatic nitro compound is introduced into the autoclave in a constant current. In the autoclave hydrogenation proceeds smoothly and rapidly.

After hydrogenation is completed, the used catalyst is recovered from the reaction mixture by a generally accepted process, for example decantation and filtration, The dehalogenation inhibitor has been also partly hydrogenated, but as far as it remains in the reaction phase, its excellent effect is maintained. Detection and analysis of dicyandiamide are performed by liquid chromatography, thin layer chromatography and infrared absorption spectrography.

The inert solvent is separated from the reaction product by distillation.

The water phase, including the dehalogenation inhibitor and its hydrogenated products dissolved therein is separated from the oil phase of the reaction product. If the reaction product is soluble in water, distillation is needed to separate water from the reaction product. Dicyandiamide and its hydrogenated products are scarcely evaporated or sublimed by heating. So by distillation, they are not substantially mixed with the distillate.

The reaction product is purified by distillation, or crystallization. The Raney nickel catalyst is used repeatedly for further hydrogenation, and, if necessary, a small amount of new catalyst is added to the used catalyst. The catalyst consumption is less than 1 percent of the hydrogenated product.

The hydrogenation of the invention may be carried out continuously.

Representative examples further illustrating the present invention follow.

EXAMPLE 1 o-chloroaniline 30.0 g of o-chloronitrobenzene (containing 0.08 percent of p-chloronitrobenzene),
90 ml of methanol,
0.8 g of Raney nickel catalyst (made from 2.0 g of alloy powder) and
0.84 g of dicyandiamide were fed into a 300 ml capacity autoclave equipped with a turbine type agitator and the air was displaced with hydrogen.

The autoclave was then pressured with hydrogen to 6 kg/cm$^2$ (gauge), the agitator was started, and the temperature was raised to 120° ± 2°C and maintained there by cooling from outside. When the pressure was reduced to 6 kg/cm$^2$ (gauge), (the hydrogen pressure 1.7 kg/cm$^2$ absolute, methanol pressure 5.3 kg/cm$^2$ abs.) by hydrogenation, hydrogen was introduced again into the autoclave and the pressure was elevated to 10 kg/cm$^2$ (gauge), (the hydrogen pressure 5.7 kg/cm$^2$ abs.) After such operation was repeated for 15 minutes, the hydrogen absorption was completed. The autoclave was cooled to room temperature. The reaction product in the autoclave was alkaline and showed pH 12.7. The Raney nickel catalyst used was separated by decantation. The decanted liquor was filtered from suspended catalyst and methanol was separated by distillation. Water (which was one of the product of hydrogenation of the nitro compound) and said dehalogenation inhibitor (some percentage of the inhibitor was generally hydrogenated) were separated from oil phase of o-chloroaniline produced.

The yield of o-chloroaniline was 23.9 g. (98.4 of theoretical). By gas chromatography, the product content was as follows:

| | |
|---|---|
| o-chloroaniline | 99.87% |
| aniline | 0.05% |
| p-chloroaniline | 0.08% |

Example for comparison 1—1

30.0 g of o-nitrochlorobenzene,
90 ml of methanol and
0.8 g of Raney nickel catalyst
were fed into the 300 ml capacity autoclave used in Example 1 and hydrogenated just as in Example 1. In this example dehalogenation inhibitor was not used. Hydrogenation temperature and pressure were almost the same with Example 1. But when hydrogenation was started, hydrogen absorption decreased by and by and stopped at last after thirty minutes. Then, the autoclave was cooled. The reaction product showed pH 5.0. By gas chromatography the product content was as follows:

| | |
|---|---|
| Aniline | 2.23% |
| o-chloroaniline | 44.26% |
| o-chloronitrobenzene | 53.43% |
| p-chloronitrobenzene and p-chloroaniline | 0.08% |

Example for comparison 1-2

30.0 g of o-chloronitrobenzene,
90 ml of methanol and
1.2 g of Raney nickel catalyst
were fed into the 300 ml capacity autoclave used in Example 1. The autoclave was then pressured with hydrogen to 10 kg/cm$^2$ and the agitator was started. The temperature was raised and adjusted to 100°C and kept in the range of ± 2°C throughout the reaction. It required 2 hours and 27 minutes to complete hydrogen absorption. After the completion, the hydrogenated product showed pH 4.0.

The yield of the product was 23.4 g.

By gas chromatography the product content was as follows:

| | |
|---|---|
| aniline | 7.37% |
| o-chloroaniline | 92.55% |
| p-chloroaniline | 0.08% |

EXAMPLE 2 p-chloroaniline 30.0 g of p-chloronitrobenzene (containing 1.20% of o-chloronitrobenzene),
90 ml of methanol,
0.8 g of Raney nickel catalyst (as mentioned in Example 1) and
0.84 g of dicyandiamide
were fed into the 300 ml capacity autoclave used in Example 1. The pressure was raised to 10 kg/cm$^2$ with hydrogen and agitation was started.

The temperature was elevated and adjusted to 120°C and kept in the range of ± 2°C, and 18 minutes were needed to complete the hydrogen absorption.

Then, the temperature was kept at 120°C for another 5 minutes and then the autoclave was cooled with water and the reaction product was separated from the catalyst at about 30°C.

The reaction product showed pH 12.9.

By gas chromatography, the product content was as follows:

| | |
|---|---|
| aniline | 0.02% |
| p-chloroaniline | 98.78% |
| o-chloroaniline | 1.20% |

Example for comparison 2

30.0 g of p-chloronitrobenzene (containing 1.20% of o-chloronitrobenzene),
90 ml of methanol and
0.8 g of Raney nickel catalyst
were fed into the autoclave mentioned in Example 2, pressured with hydrogen to 10 kg/cm$^2$ and stirred. The hydrogenation was carried out at 120° ± 2°C, 10 kg/cm$^2$. After 18 minutes of reaction, the hydrogen absorption stopped.

Then, the reaction mixture was kept at 120°C for another 5 minutes and cooled to 30°C. The hydrogenated product showed pH 4.7.

By gas chromatography, the product content was as follows:

| | |
|---|---|
| aniline | 5.94% |
| p-chloroaniline | 92.87% |
| o-chloroaniline | 1.19% |

EXAMPLE 3 2.5-dichloroaniline 30.0 g of 2.5-dichloronitrobenzene (containing p-chloronitrobenzene 0.07% o-chloronitrobenzene 0.04% 3.4-dichloronitrobenzene 0.14%),
90 ml of methanol,
0.8 g of Raney nickel catalyst and
0.84 g of dicyandiamide
were fed into the 300 ml capacity autoclave used in Example 1. It was then pressured with hydrogen to 10 kg/cm$^2$ and the agitation was started. The temperature was elevated and adjusted to 120° ± 2°C. The hydrogenation was carried out at this temperature and completed after 18 minutes. The reaction product showed pH 12.9.

By gas chromatography the product content was as follows:

| | |
|---|---|
| aniline | trace |
| o-chloroaniline | 0.04% |
| p-chloroaniline | 0.07% |
| 3,4-dichloroaniline | 0.14% |
| 2,5-dichloroaniline | 99.75% |

Example for comparison 3

30.0 g of 2,5-dichloronitrobenzene,
90 ml of methanol and
0.8 g of Raney nickel catalyst
were fed into the autoclave mentioned in Example 3.

It was then pressured with hydrogen to 10 kg/cm² and the agitation was started.

The temperature was elevated and adjusted to 120° ± 2°C. The absorption of hydrogen stopped after 18 minutes. The hydrogenated product showed pH 3.9.

By gas chromatography the product content was as follows:

| | |
|---|---|
| p-chloroaniline | 0.05% |
| o-chloroaniline | 0.04% |
| m-chloroaniline | 0.07% |
| 3,4-dichloroaniline | 0.13% |
| 2,5-dichloroaniline | 69.25% |
| 2,5-dichloronitrobenzene | 30.46% |

EXAMPLE 4 o-bromoaniline 38.5 g of o-bromonitrobenzene (containing 0.80% of p-bromonitrobenzene),
90 ml of methanol,
0.8 g of Raney nickel catalyst and
0.84 g of dicyandiamide
were fed into the 300 ml capacity autoclave used in Example 1 and hydrogenated under a pressure of 10 kg/cm² at about 100° ∼ 105°C. The reaction was completed after 29 minutes. The reaction product showed pH 12.7.

By gas chromatography, the composition of the product was shown as follows:

| | |
|---|---|
| aniline | 0.19% |
| o-bromoaniline | 99.02% |
| p-bromoaniline | 0.79% |

The yield of the product was 32.0 g (98% of theoretical).

Example for comparison 4

38.5 g of o-nitrobromobenzene (containing 0.80% of p-isomer),
90 ml of methanol and
0.8 g of Raney nickel catalyst
were fed into the autoclave used in Example 4 and hydrogenated under a pressure of 10 kg/cm² at about 100° ∼ 105°C. After 30 minutes of reaction, the hydrogen absorption stopped. Then, after maintained at the same temperature for 5 minutes, the reaction mixture was cooled and analyzed by gas chromatography as follows:

| | |
|---|---|
| aniline | 5.28% |
| o-bromoaniline | 23.04% |
| p-bromoaniline | 0.21% |
| o-bromonitrobenzene | 70.88% |
| p-bromonitrobenzene | 0.59% |

EXAMPLE 5 3,4-dichloroaniline 36.6 g of 3,4-dichloronitrobenzene (containing 1.84% of 2,3-dichloronitrobenzene),
90 ml of methanol,
0.8 g of Raney nickel catalyst and
0.84 g of dicyandiamide
were fed into the autoclave used in Example 4 and hydrogenated under a pressure of 10 kg/cm² at about 115° ∼ 120°C. The reaction was completed after 16 minutes. The reaction product showed pH 12.2. The composition of the product was shown by gas chromatography as follows:

| | |
|---|---|
| aniline | trace (under 0.01%) |
| monochloroaniline | 0.01% |
| 3,4-dichloroaniline | 98.15% |
| 2,3-dichloroaniline | 1.84% |

The yield of the product was 30.4 g (98.5% of theoretical).

Example for comparison 5

36.6 g of 3,4-dichloronitrobenzene (containing 1.84% of 2,3-dichloronitrobenzene),
90 ml of methanol and
0.8 g of Raney nickel catalyst
were fed into the autoclave used in Example 5 and hydrogenated under a pressure of 10 kg/cm² at about 115° ∼ 120°C as mentioned in Example 5. After 23 minutes of reaction, the hydrogen absorption stopped. The reaction mixture was kept at the same temperature for 3 minutes. Then the agitation was stopped and the reaction mixture was cooled. The reaction product showed pH 3.9.

The composition of the product was shown by gas chromatography as follows:

| | |
|---|---|
| aniline | 0.23% |
| m- and p-chloroaniline | 4.04% |
| 3,4-dichloroaniline | 93.02% |
| 2,5-dichloroaniline | 1.80% |
| others having higher boiling point | 0.91% |

EXAMPLE 6 2,4-diaminochlorobenzene 30.0 g of 2,3-dinitrochlorobenzene (containing a small amount of isomers),
90 ml of methanol,
1.2 g of Raney nickel catalyst and
0.84 g of dicyandiamide
were fed into the autoclave used in Example 5 and hydrogenated under a pressure of 10 kg/cm² at about 80° ± 2°C. The absorption of hydrogen was completed after 87 minutes.

The solution of the reaction product showed pH 10.7.

The composition of the product was analyzed by gas chromatography as follows:

| | |
|---|---|
| m-phenylenediamine | 0.03% |
| 2,4-diaminochlorobenzene | 98.88% |
| diaminochlorobenzene isomers | 0.52% |
| other reaction products | 0.57% |

The yield of the product was 20.6 g (97.6% of the theoretical).

Example for comparison 6

30.0 g of 2,4-dinitrochlorobenzene,
90 ml of methanol and
1.2 g of Raney nickel catalyst
were fed into the autoclave used in Example 6 and hydrogenated under a pressure of 10 kg/cm² at about 80° ± 2°C. After 76 minutes of reaction, the hydrogen absorption stopped. The reaction product showed pH 4.7.

The composition of the product was as follows:

| | |
|---|---|
| m-phenylenediamine | 17.99% |
| 2,4-diaminochlorobenzene | 80.93% |
| diaminochlorobenzen isomers | 0.50% |
| other reaction products | 0.58% |

EXAMPLE 7 O-chloroaniline 30.0 g of o-chloronitrobenzene (containing 0.08% of p-chloronitrobenzene),
90 ml of methanol,
0.8 g of Raney nickel catalyst and
1.68 g of calcium cyanamide were fed into the autoclave used in Example 1 and hydrogenated under a pressure of 10 kg/cm$^2$ at about 85° ± 2°C. The hydrogen absorption was completed after 16 minutes. The reaction mixture was kept at the same temperature for 5 minutes and cooled to room temperature.

The reaction product showed pH 11.5.

The composition of the product was analyzed by gas chromatography as follows:

| | |
|---|---|
| aniline | 0.09% |
| o-chloroaniline | 99.83% |
| p-chloroaniline | 0.08% |

The yield of the product was 30.4 g (98.5% of theoretical)

EXAMPLE 8

A 5,000—$l$ steel pressure reactor was used for hydrogenation. The reactor was equipped with two coils for heating or cooling and an agitator. 150 kg of Raney nickel catalyst and 1,250$l$ of methanol were fed into the reactor. 10 kg of dicyandiamide dissolved in 250$l$ of methanol were fed into the reactor.

The reactor was then pressured with hydrogen to 12 kg/cm$^2$ and the agitator was started. The temperature was adjusted to 80°C ± 2°C. Molten o-chloronitrobenzene (containing o-chloronitrobenzene 99.79%, p-chloronitrobenzene 0.19% and other impurities 0.02%) was fed continuously into the reactor through a plunger pump. The pressure was kept at 12 kg/cm$^2$, while the temperature was kept at 80° ± 2°C.

1576 kg of o-chloronitrobenzene were fed during 5 hours. After feeding of o-chloronitrobenzene was completed the mixture was continuously stirred at the same temperature for 30 minutes and cooled with water passed through the coils. Agitation was stopped when the reaction mixture was cooled at 40°C.

The reaction mixture was allowed to stand for 2 ~ 3 hours and the catalyst was separated from the liquid by a generally accepted process, for example, decantation and filtration.

The reaction product showed pH 12.7.

By gas chromatography the composition of the product was shown as follows:

| | |
|---|---|
| aniline | 0.02% |
| o-chloroaniline | 99.77% |
| p-chloroaniline | 0.19% |
| other impurities | 0.02% |

The yield of the product was 1237 kg (97% of theoretical)

EXAMPLE 9.

30.0 g of o-chloronitrobenzene,
90 ml of methanol,
0.8 g of Raney nickel and
0.03 g of dicyandiamide were fed into the 300 ml capacity autoclave used in Example 1. The autoclave was pressured with hydrogen to 10 kg/cm$^2$ and the agitator was started. The temperature was raised and adjusted to 50°C and kept within the range of ± 2°C throughout the reaction.

The pressure was kept in the range of 8–10 kg/cm$^2$ during the hydrogenation.

It took 2 hours and 19 minutes to complete the hydrogenation. After completion the reaction product was kept at the same temperature for 5 minutes, then cooled to 40°C and the pressure was reduced. By gas chromatography, the product content was as follows:

| | |
|---|---|
| aniline | 0.11% |
| o-chloroaniline | 99.79% |
| p-chloroaniline | 0.07% |
| Other compounds originating from impurities of o-chloronitrobenzene | 0.03% |

EXAMPLE 10.

30.0 g of o-chloronitrobenzene
90 ml of methanol
0.8 g of Raney nickel and
15 g of dicyandiamide were fed into the 300 ml capacity autoclave used in Example 1. The hydrogenation was proceeded under the hydrogen pressure of 8–10 kg/cm$^2$ at 120° ± 2°C. At this temperature, it took 25 minutes to complete the hydrogenation.

After completion the reaction product was kept at the same temperature for 5 minutes, then cooled to 40°C and the pressure was reduced.

By gas chromatography, the product content was as follows:

| | |
|---|---|
| aniline | 0.10% |
| o-chloroaniline | 99.36% |
| p-chloroaniline | 0.08% |
| higher boiling point products originating from the hydrogenation in existence of dicyandiamide | 0.46% |

EXAMPLE 11.

30.0 g of o-chloronitrobenzene
90 ml of methanol
0.8 g of Raney nickel and
1.0 g of cyanamide were fed into the autoclave used in Example 1 and hydrogenated under the pressure of 10 kg/cm$^2$ at about 90° ± 2°C. The hydrogen absorption was completed in 139 minutes. The reaction mixture was kept at the same temperature for 5 minutes and cooled to 40°C. The product showed pH 12.7. The composition of the product was analyzed by gas chromatography as follows:

| | |
|---|---|
| aniline | 0.11% |
| o-chloroaniline | 99.13% |
| p-chloroaniline | 0.08% |
| higher boiling point products originating from | |

-continued

| cyanamide | 0.68% |
|---|---|

EXAMPLE 12.

30.0 g of 5-chloro-2-nitroanisole
90 ml of methanol
0.8 g of Raney nickel and
0.84 g of dicyandiamide were fed into the autoclave used in Example 1 and hydrogenated under the pressure of 10 kg/cm$^2$ at about 95° ± 2°C.

The hydrogen absorption was completed in 35 minutes. The reaction mixture was kept at the same temperature for 5 minutes and cooled to 40°C. The product showed pH 11.9. The composition of the product was analyzed by gas chromatography as follows:

| o-anisidine | trace (less than 0.01%) |
|---|---|
| 5-chloro-2-amino-1-methoxybenzene | 99.93% |
| other hydrogenated products originating from the impurities of the chloro-nitro compound | 0.07% |

Example for comparison 12.

30.0 g of 5-chloro-2-nitroanisole
90 ml of methanol and
0.8 g of Raney nickel were fed into the autoclave used in Example 1 and hydrogenated under the pressure of 10 kg./cm$^2$ at about 95° ± 2°C.

The hydrogen absorption was completed in 40 minutes. The reaction mixture was kept at the same temperature for 5 minutes and cooled to 40°C. The product showed pH 6.7. The composition of the product was analyzed by gas chromatography as follows:

| o-anisidine | 0.98% |
|---|---|
| 5-chloro-2-amino-1-methoxybenzene | 98.57% |
| other hydrogenated products originating from the chloronitro-compound | 0.45% |

EXAMPLE 13.

20.0 g of 2-chloro-6-nitrotoluene
90 ml of methanol
0.8 g of Raney nickel and
1.0 g of dicyandiamide were fed into the autoclave used in Example 1 and hydrogenated under the pressure of 10 kg/cm$^2$ at about 80° ± 2°C.

The hydrogen absorption was completed in 17 minutes. The reaction mixture was kept at the same temperature for 5 minutes and cooled to 40°C.

The composition of the product was analyzed by gas chromatography as follows:

| o-toluidine | 0.03% |
|---|---|
| 2-chloro-6-aminotoluene | 99.87% |
| *o-choroaniline | 0.03% |
| *p-chloroaniline | 0.07% |

Note:
*These originate from the impurities of chloronitrotoluene.

EXAMPLE 14.

10.0 g of 4-chloro-2-nitrophenol
150 ml of methanol
0.8 g of Raney nickel and
1.0 g of dicyandiamide were fed into the autoclave used in Example 1 and hydrogenated under the pressure of 10 kg/cm$^2$ at about 50° ± 2°C.

The hydrogen absorption was completed in 5 minutes.

The reaction mixture was kept at the same temperature for further 15 minutes and then the stirring was stopped. The reaction mixture was separated from Raney nickel in an ordinary way.

The reaction product was analyzed by liquid chromotography. The purity of 4-chloro-2-animophenol was 99% and it contained 1% of impurity. It was supposed to be a chloroaminophenol isomer originating from the chloronitrophenol.

EXAMPLE 15.

26.5 g of 2,5-dichloro-4-nitroaniline (melting point: 156°–157°C)
180 ml of methanol
1.1 g of Raney nickel and
1.6 g of dicyandiamide were fed into the 300 ml capacity autoclave used in Example 1. The autoclave was pressured with hydrogen to 10 kg/cm$^2$ and the agitator was started. The temperature was raised and adjusted to 90°C and kept within the range of ± 2°C throughout the reaction. The pressure was kept in the range of 8–10 kg/cm$^2$ during the hydrogenation.

It took 30 minutes to complete the hydrogenation. After completion, the reaction product was kept at the same temperature for 10 minutes.

Then, the solution of the reaction product was filtered off from the catalyst under the pressure at 8 kg/cm$^2$, at 85°C. The catalyst sludge was left in the autoclave. Methanol was distilled off from the solution.

21.0 g (92.6% of the theoretical yield) of greyish white crystal (melting point: 167° – 168°C) was obtained by crystallization from the aqueous solution. By gas chromatography, the purity of the crystal was 99.8% of the theoretical value.

EXAMPLE 16.

5.0 g of 2,4,5-trichloronitrobenzene
90 ml of methanol
0.8 g of Raney nickel and
0.84 g of dicyandiamide were fed into the autoclave used in Example 1 and hydrogenated under a pressure of between 6 and 8 kg/cm$^2$ at about 70° ± 2°C. The hydrogen absorption was completed after 13 minutes. The reaction mixture was kept at the same temperature for 3 minutes and cooled to 40°C. The product showed pH 9.8. The yield of 2,4,5-trichloroaniline was 95.2% of the theoretical. The composition of the product was analyzed by the gas chromatography as follows:

| 2,4,5-trichloroaniline | 99.96% |
|---|---|
| dichloroaniline | 0.03% |
| 2,4,5-trichloronitrobenzene | trace |

Example for comparison 16

50 g of 2,4,5-trichloronitrobenzene
90 ml of methanol and
08 g of Raney nickel were fed into the autoclave used in Example 1 and hydrogenated under a pressure of between 6 and 8 kg/cm$^2$ at about 70° ± 2°C. The hydrogen absorption stopped after 18 minutes. The reaction mixture was kept at the same temperature for 3 minutes and cooled to 40°C.

The product showed pH 3.2.

The composition of the product was analyzed by gas chromatography as follows:

| | |
|---|---|
| 2,4,5-trichloronitrobenzene | 2.27% |
| dichloroanilines | 4.88% |
| other by-products | 0.89% |
| 2,4,5-trichloroaniline | 91.96% |

What we claim is:

1. A process for the production of halogenated aromatic primary amines by catalytic hydrogenation of halogenated aromatic nitro compounds, which comprises hydrogenating a halogenated aromatic nitro compound in the presence both of Raney nickel and of a dehalogenation inhibitor selected from the group consisting of dicyandiamide, cyanamide and calcium cyanamide, in an inert solvent at a temperature in the range from 40° to 150°C under an elevated hydrogen pressure.

2. A process as claimed in claim 1 wherein the amount of dicyandiamide is from 0.03 to 30% by weight of halogenated aromatic nitro compound.

3. A process as claimed in claim 1 wherein the amount of cyanamide is from 0.03 to 30% by weight of halogenated aromatic nitro compound.

4. A process as claimed in claim 1 wherein the amount of calcium cyanamide is from 0.1 to 30% by weight of halogenated aromatic nitro compound.

5. A process as claimed in claim 1 wherein the temperature is from 60° to 130°C.

6. A process as claimed in claim 1 wherein the hydrogen pressure is from 1 to 100 kg/cm$^2$.

7. A process as claimed in claim 1 wherein Raney nickel is used in a quantity from 0.5 to 20% by weight of halogenated nitro compound.

8. A process as claimed in claim 1 wherein the halogenated aromatic primary amine is an amine selected from the group consisting of chloroanilines, bromoanilines, dichloroanilines, trichloroanilines, dichlorodiaminobenzenes, chlorotoluidines, diaminochlorobenzenes, chloromethoxyanilines, and chloroaminophenols.

* * * * *